(12) United States Patent
Huber

(10) Patent No.: US 12,736,452 B2
(45) Date of Patent: Sep. 15, 2026

(54) ALCOHOL AND SUGAR CONTENT MEASURING DEVICE

(71) Applicant: TrueDyne Sensors AG, Reinach (CH)

(72) Inventor: Christof Huber, Bern (CH)

(73) Assignee: TrueDyne Sensors AG, Reinach (CH)

( * ) Notice: Subject to any disclaimer, the term of this patent is extended or adjusted under 35 U.S.C. 154(b) by 196 days.

(21) Appl. No.: 18/717,614

(22) PCT Filed: Nov. 21, 2022

(86) PCT No.: PCT/EP2022/082645
§ 371 (c)(1),
(2) Date: Jun. 7, 2024

(87) PCT Pub. No.: WO2023/110306
PCT Pub. Date: Jun. 22, 2023

(65) Prior Publication Data
US 2025/0052654 A1 Feb. 13, 2025

(30) Foreign Application Priority Data
Dec. 13, 2021 (DE) ..................... 10 2021 132 835.7

(51) Int. Cl.
*G01N 9/26* (2006.01)
*G01N 33/14* (2006.01)

(52) U.S. Cl.
CPC ............. *G01N 9/26* (2013.01); *G01N 33/143* (2013.01); *G01N 33/146* (2013.01)

(58) Field of Classification Search
CPC ............. G01N 9/002; G01N 2009/006; G01N 11/16; G01N 2291/02818;
(Continued)

(56) References Cited

U.S. PATENT DOCUMENTS 11,326,996 B2 * 5/2022 Wells .................. G01N 29/326
2015/0096385 A1 4/2015 Downie et al.
(Continued)

FOREIGN PATENT DOCUMENTS

AT 514574 B1 * 2/2015 ............. G01N 9/002
DE 69315320 T2 6/1998
(Continued)

OTHER PUBLICATIONS

Fortin, T., et al., Advanced calibration, adjustment, and operation of a density and sound speed analyzer, J. Chem. Thermodynamics, v. 57, pp. 276-285 (2013).
(Continued)

*Primary Examiner* — Andre J Allen
(74) *Attorney, Agent, or Firm* — Christopher R. Powers; Endress+Hauser (USA) Holding, Inc.

(57) ABSTRACT

A measuring apparatus for measuring a property of a medium includes: a density instrument for measuring a density of the medium; a speed of sound instrument for measuring a speed of sound in the medium; a temperature device for measuring a temperature of the medium; and an electronic circuit, wherein the foregoing components are arranged in a housing wherein the speed of sound instrument includes a pressure measuring cell, wherein the electronic circuit is configured to determine a compressibility from pressure measurements for at least two different pressure measuring cell volumes and to determine a speed of sound in the medium from the compressibility, wherein side surfaces of the pressure measuring cell each have a surface area of at most 0.5 square centimeter, and wherein the pressure measuring cell has a maximum volume of less than 5 cubic centimeters.

14 Claims, 2 Drawing Sheets

(58) Field of Classification Search
CPC ............. G01N 2009/004; G01N 33/14; G01N 33/143; G01N 33/146; G01N 9/26; G01N 11/04; G01N 2291/014; G01N 2291/024; G01N 25/02; G01N 29/02; G01N 29/022; G01N 29/036; G01N 29/222; G01N 35/00623; G01N 7/00
See application file for complete search history.

(56) References Cited

U.S. PATENT DOCUMENTS

| | | | | |
|---|---|---|---|---|
| 2020/0355438 | A1 | 11/2020 | Höcker | |
| 2024/0191162 | A1* | 6/2024 | Sáenz-Díez Muro | C12G 1/02 |
| 2024/0254417 | A1* | 8/2024 | Glucina | G01F 23/14 |
| 2025/0258152 | A1* | 8/2025 | Crabtree | C12G 3/07 |

FOREIGN PATENT DOCUMENTS

| | | | | |
|---|---|---|---|---|
| DE | 102014001165 | A1 | 6/2015 | |
| DE | 102016112002 | A1 * | 1/2018 | G01F 25/10 |
| DE | 102018127526 | A1 | 5/2020 | |
| DE | 102021105400 | A1 * | 9/2022 | G01F 1/8404 |
| DE | 102021132829 | A1 * | 6/2023 | G01N 9/04 |
| EP | 1771705 | B1 | 11/2018 | |
| JP | 2018200240 | A * | 12/2018 | |
| TW | M469481 | U * | 1/2014 | |

OTHER PUBLICATIONS

Jablonska, Jana, Compressibility of the fluid, EPJ Web of Conferences, v. 67, 02048 (2014) (https://www.epj-conferences.org/articles/epjconf/abs/2014/04/epjconf_efm-13_02048/epjconf_efm-13_02048.html, last accessed Jun. 3, 2024).

* cited by examiner 1 70 50 20 50 10 50 30 / 31 30 / 31 40 60 71 61 / 62 / 63

21
22
20
21.1
50
50
24
24
21.2
21.3 / 21.4
23
21.2

ALCOHOL AND SUGAR CONTENT MEASURING DEVICE

CROSS-REFERENCE TO RELATED APPLICATIONS

The present application is related to and claims the priority benefit of German Patent Application No. 10 2021 132 835.7, filed Dec. 13, 2021, and International Patent Application No. PCT/EP2022/082645, filed Nov. 21, 2022, the entire contents of which are incorporated herein by reference.

TECHNICAL FIELD

The invention relates to a measuring apparatus for measuring at least one media property of a medium, in particular a beverage, such as an alcohol and/or sugar content.

BACKGROUND

Typically, a plurality of measuring instruments are used, such as a density measuring instrument and a speed of sound measuring instrument, in order to derive a statement about the alcohol or sugar content from the density and speed of sound measured values.

DE102014001165A1 shows an exemplary speed of sound measuring instrument by means of ultrasonic transducers.

The disadvantage of the prior art is that the necessary measured values have to be obtained via a plurality of separate measuring instruments and then combined.

SUMMARY

The object is achieved by a measuring apparatus according to the present disclosure.

The object is achieved by a measuring apparatus according to independent claim 1.

With a measuring apparatus according to the invention for measuring at least one media property of a medium such as a beverage,

- the measuring apparatus comprises a density measuring instrument for measuring a density of the beverage, a speed of sound measuring instrument for measuring a speed of sound in the beverage, a temperature measuring device for measuring a temperature of the beverage and an electronic measuring/operating circuit,
- wherein the density measuring instrument, the speed of sound measuring instrument, the temperature measuring device and the electronic measuring/operating circuit are arranged in a housing of the measuring apparatus,
- wherein the electronic measuring/operating circuit is configured to operate the density measuring instrument, the speed of sound measuring instrument and the temperature measuring device and to determine an alcohol and/or sugar content and/or a type of sugar of the beverage by means of measured density values, speed of sound measured values and temperature measured values,
- characterized in that
- the speed of sound measuring instrument comprises at least one pressure measuring cell and an adjustable pressure piston, by means of which a volume of the pressure measuring cell can be adjusted,
- wherein the electronic measuring/operating circuit is configured to determine a compressibility from pressure measurements for at least two different pressure measuring cell volumes and to determine a speed of sound in the medium from said compressibility,
- wherein side surfaces of the pressure measuring cell each have a surface area FI of at most 3 and preferably at most 2 square centimeters, wherein the side surfaces each have a maximum extent MA, in which case $MA=F*FI^{0.5}$ where $F<5$,
- wherein the pressure measuring cell has a maximum volume of less than 5 cubic centimeters, and in particular less than 3 cubic centimeters, and preferably less than 1 cubic centimeter.

In one embodiment, the piston can be positioned in a defined manner by means of stops or by means of a screwing apparatus.

In this way, the determination of the speed of sound is less prone to error.

In one embodiment, the stops are configured by means of a bayonet system.

In one embodiment, two hoses are connected to the speed of sound measuring instrument for the purpose of supplying and discharging media, wherein the hoses have a maximum diameter of 4 millimeters and a maximum length of 10 centimeters,

- wherein the pressure measuring cell can be closed in a pressure-tight manner by means of at least one valve.

In one embodiment, the density measuring instrument has a media-carrying density measuring channel,

- wherein the density measuring instrument is configured to excite the density measuring channel to oscillations and to determine a density of the beverage based on a resonance frequency of the density measuring channel to be determined,
- or wherein the density measuring instrument has an oscillating apparatus that projects into the density measuring channel, wherein the density measuring instrument is configured to excite the oscillating apparatus to oscillate and to determine a density of the beverage based on a resonance frequency of the oscillating apparatus to be determined.

In one embodiment, two hoses are connected to the density measuring channel for the purpose of supplying and discharging media, wherein hoses have a maximum diameter of 4 millimeters and a maximum length of 10 centimeters.

In one embodiment, a resonance frequency of the density measuring channel or the oscillating apparatus is greater than 10 KHz in the unloaded state.

In this way, a sufficient compactness of the density measuring instrument is ensured.

In one embodiment, the temperature measuring device has in each case one temperature sensor for the density measuring instrument and one for the speed of sound measuring instrument.

The small measuring volumes of the speed of sound measuring instrument and density measuring instrument mean that uneven heating of the housing, for example by carrying the measuring apparatus by hand, heats the medium unevenly. By providing separate temperature measured values, the electronic measuring/operating circuit can use correct temperature measured values for the determination of density and speed of sound.

In one embodiment, the electronic measuring/operating circuit is arranged in a first housing chamber of the housing, wherein the density measuring instrument, the speed of sound measuring instrument and the temperature measuring device are arranged outside the first housing chamber in the housing.

In this way, a heat output of the electronic measuring/operating circuit can be limited. The heat output is then transferred to an environment via a housing wall instead of to the density measuring instrument and the speed of sound measuring instrument.

In one embodiment, the measuring apparatus can be carried by hand.

In one embodiment, the measuring apparatus has a reading instrument for classifying measurement samples, such as a barcode reading instrument, an RFID reading instrument or a QR code reading instrument.

In this way, work processes can be greatly simplified in a laboratory, for example.

BRIEF DESCRIPTION OF THE DRAWINGS

The invention will now be described with reference to exemplary embodiments, figures of which include.

DETAILED DESCRIPTION

Figures 1, 2A, 2B:
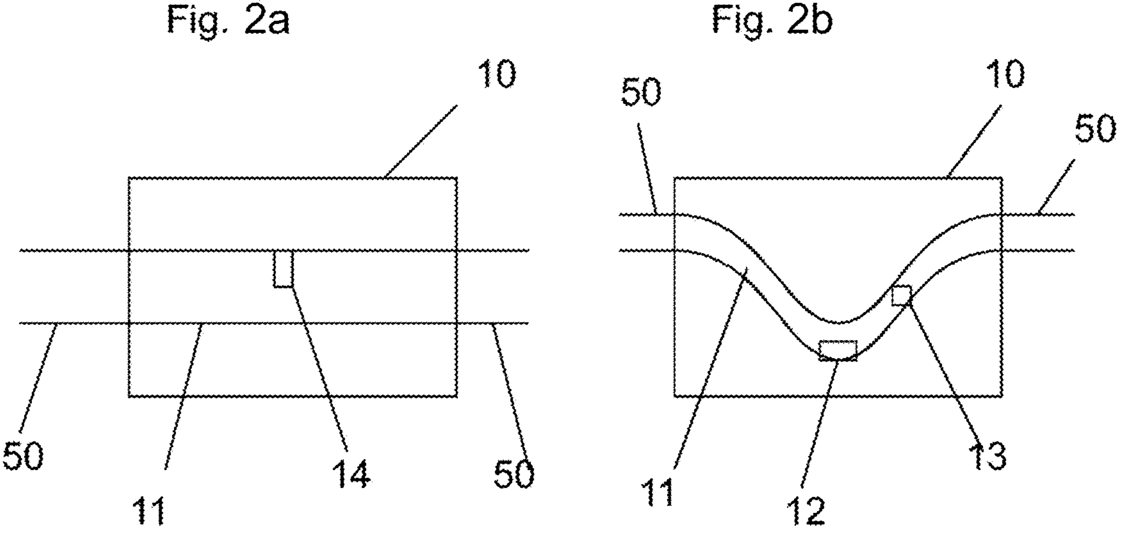
FIG. 1 shows a schematic structure of an exemplary measuring apparatus according to the invention present disclosure.
FIGS. 2*a* and 2*b* show two exemplary density measuring instruments, respectively.

FIG. 1 outlines an exemplary measuring apparatus 1 according to the invention for measuring at least one media property of a medium such as a beverage, which measuring apparatus comprises a housing 70 in which a density measuring instrument 10, a speed of sound measuring instrument 20, a temperature measuring device 30 and an electronic measuring/operating circuit 40 are arranged. The density measuring instrument is configured to determine the density of a beverage or medium by means of the electronic measuring/operating circuit, and the speed of sound measuring instrument is configured to determine the speed of sound in the beverage. For this purpose, the electronic measuring/operating circuit 40 is configured to operate the density measuring instrument, the speed of sound measuring instrument and the temperature measuring device. The temperature measuring device is used to determine the temperature of the medium or beverage. The sugar content and/or alcohol content of the beverage can be determined from the density, speed of sound and temperature.

As shown here, the temperature measuring device 30 can have two temperature sensors 31, in order to detect the temperature of the medium or beverage in the density measuring instrument and in the speed of sound measuring instrument. In this way, the influence of temperature on density and speed of sound can be better detected.

As shown here, the housing 70 can have a first housing chamber, in which the electronic measuring/operating circuit 40 can be arranged separately from the speed of sound measuring instrument and density measuring instrument. In this way, the heating due to the electronic measuring/operating circuit of the speed of sound measuring instrument and density measuring instrument can be limited.

Furthermore, the measuring apparatus 1 can also have a reading instrument 60 for classifying measurement samples, such as a barcode reading instrument 61, an RFID reading instrument 62 or a QR code reading instrument 63. This can greatly simplify work in the laboratory, for example.

In particular, the measuring apparatus is designed to be able to be carried by hand.

FIG. 2*a* illustrates a density measuring instrument 10, with which an oscillating apparatus 14 projects into a measuring channel for guiding the medium. The medium is fed to and discharged from the density measuring instrument through a hose 50. A dependence of the resonance frequency of the oscillating apparatus on the density of the medium is used to determine the density of the medium.

Alternatively, as shown in FIG. 2*b*, the measuring channel can be excited to oscillations by means of an oscillation exciter 12, which is detected, for example, by means of an oscillation sensor 13. Here as well, a resonance frequency, here that of the measuring channel, is dependent on the density of the medium, so that the density can be deduced from the resonance frequency.

Figure 3:
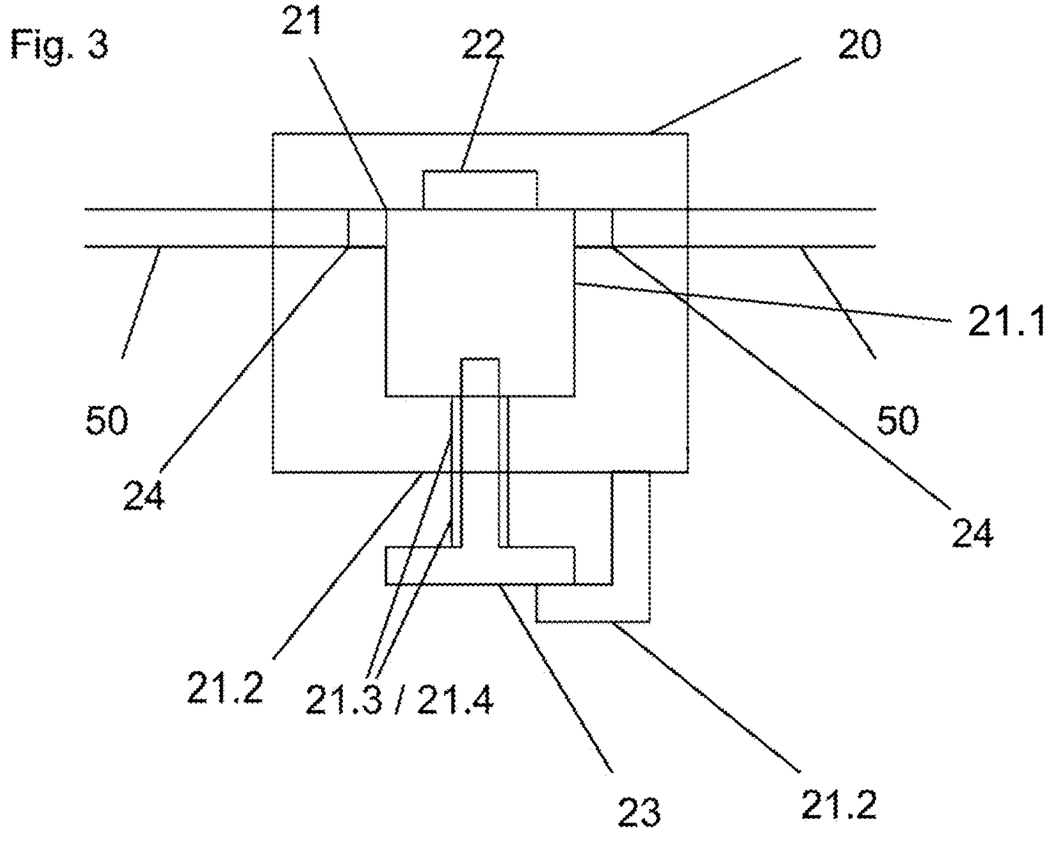
FIG. 3 shows an exemplary speed of sound measuring instrument according to the present disclosure.

FIG. 3 outlines a structure of an exemplary speed of sound measuring instrument 20 according to the invention. The speed of sound measuring instrument comprises at least one pressure measuring cell 21 with a pressure sensor 22 and an adjustable pressure piston 23, by means of which a volume of the pressure measuring cell can be adjusted.

The electronic measuring/operating circuit 40 is configured to determine a compressibility from pressure measurements for at least two different pressure measuring cell volumes and different pressures resulting therefrom and to determine a speed of sound in the medium from said compressibility, wherein side surfaces of the pressure measuring cell each have a surface area FI of at most 0.5 square centimeter, wherein the side surfaces each have a maximum extent MA, in which case MA=F*FI^0.5 where F<5, wherein the pressure measuring cell has a maximum volume of less than 5 cubic centimeters, and in particular less than 3 cubic centimeters, and preferably less than 1 cubic centimeter.

Two hoses 50 are connected to the speed of sound measuring instrument 20 for the purpose of supplying and discharging media, wherein the hoses have a maximum diameter of 4 millimeters and a maximum length of 10 centimeters, wherein, as shown here, the pressure measuring cell can be closed in a pressure-tight manner by means of two valves 24.

In one embodiment, the pressure piston 23 can be positioned in two defined positions by means of stops 21.2. Thus, two precisely known volumes can be adjusted. In this way, the determination of the speed of sound is less prone to error. The stops 21.2 can also be configured by means of a bayonet system, for example. Alternatively or additionally, as shown here, a screwing apparatus 21.3 can also be configured to adjust the two positions. For example, the piston and a wall of the pressure measuring cell can have an interlocking threaded apparatus 21.4.

A relationship between pressure change dP and volume change dV and a compression modulus K applies as follows:

$$K=-(dP^{*}V)/(dV)$$

The density D is related to the speed of sound S and the compression modulus as follows:

$$D=K/S^{\wedge}2.$$

By knowing the density and the compression modulus, the speed of sound can be calculated.

Knowing the density and the speed of sound, a person skilled in the art can draw conclusions about the alcohol content and/or sugar content and/or type of sugar of the beverage.

The invention claimed is:

1. A measuring apparatus for measuring at least one property of a medium, the measuring apparatus comprising:

a density measuring device configured to measure a density of the medium;

a speed of sound measuring device configured to measure a speed of sound in the medium, wherein the speed of sound measuring device comprises at least one pressure measuring cell, which includes a pressure sensor and an adjustable pressure piston, which is configured to enable adjustment of a volume of the at least one pressure measuring cell;

a temperature measuring device configured to measure a temperature of the medium;

an electronic measuring/operating circuit; and a housing in which the density measuring device, the speed of sound measuring device, the temperature measuring device, and the electronic measuring/operating circuit are disposed, wherein the electronic measuring/operating circuit is configured to operate the density measuring device, the speed of sound measuring device, and the temperature measuring device and to determine at least one of an alcohol, sugar content, and a type of sugar of the medium based on density measured values, speed of sound measured values, and temperature measured values of the medium, wherein the electronic measuring/operating circuit is configured to determine a compressibility of the medium from pressure measured values at at least two different pressure measuring cell volumes of the at least one pressure measuring cell and from the density measured values resulting therefrom, and to determine a speed of sound in the medium from the determined compressibility, wherein side surfaces of the at least one pressure measuring cell each have a surface area (FI) of at most 3 square centimeters ($cm^2$), wherein the side surfaces each have a maximum dimension (MA) such that:

$$MA = F \cdot FI \hat{} 0.5, \text{ where } F < 5,$$

wherein the at least one pressure measuring cell has a maximum volume of less than 5 cubic centimeters ($cm^3$).

2. The measuring apparatus according to claim 1, wherein side surfaces each have a surface area of at most 2 $cm^2$.

3. The measuring apparatus according to claim 1, wherein the at least one pressure measuring cell has a maximum volume of less than 1 $cm^3$.

4. The measuring apparatus according to claim 1, wherein the pressure piston is configured to be positioned in a defined manner by stops or via a screw apparatus.

5. The measuring apparatus according to claim 4, wherein the pressure piston is configured to be positioned by the stops, which are set by a bayonet system.

6. The measuring apparatus according to claim 1, wherein two hoses are connected to the speed of sound measuring device so as to supply and discharge the medium, wherein the hoses each have a maximum diameter of 4 millimeters (mm) and a maximum length of 10 cm, wherein the at least one pressure measuring cell is configured to be closed in a pressure-tight manner by at least one valve.

7. The measuring apparatus according to claim 1, wherein the density measuring device includes a density measuring channel configured to convey the medium, and wherein the density measuring device is configured to excite the density measuring channel to oscillations using an oscillation exciter and to determine the density of the medium based on a resonance frequency of the density measuring channel, which resonant frequency is determined by an oscillation sensor, or wherein the density measuring device includes an oscillating apparatus that projects into the density measuring channel, wherein the density measuring device is configured to excite the oscillating apparatus to oscillate and to determine the density of the medium based on a resonance frequency of the oscillating apparatus to be determined.

8. The measuring apparatus according to claim 7, wherein two hoses are connected to the density measuring channel and adapted to supply and discharge the medium, wherein the hoses have a maximum diameter of 4 mm and a maximum length of 10 cm.

9. The measuring apparatus according to claim 7, wherein the resonance frequency of the density measuring channel or the oscillating apparatus is greater than 10 kHz in an unloaded state.

10. The measuring apparatus according to claim 1, wherein the temperature measuring device includes a first temperature sensor for the density measuring device and a second temperature sensor for the speed of sound measuring device.

11. The measuring apparatus according to claim 1, wherein the electronic measuring/operating circuit is disposed in a first housing chamber of the housing, and wherein the density measuring device, the speed of sound measuring device and the temperature measuring device are arranged in the housing outside the first housing chamber.

12. The measuring apparatus according to claim 1, wherein the measuring apparatus is configured to be carried by hand.

13. The measuring apparatus according to claim 1, wherein the measuring apparatus includes a reading device configured to classify measurement samples, wherein the reading device includes a barcode reading device, an RFID reading device, or a QR code reading device.

14. The measuring apparatus according to claim 1, wherein the medium is a beverage.

* * * * *